(12) United States Patent
Heyl et al.

(10) Patent No.: US 10,821,034 B2
(45) Date of Patent: Nov. 3, 2020

(54) GARMENT MANUFACTURING SYSTEM AND METHOD

(71) Applicants: BioLink Systems, LLC, Covington, KY (US); University of Louisville Research Foundation, Louisville, KY (US)

(72) Inventors: Ken Heyl, Birmingham, AL (US); Doug Jackson, New Albany, IN (US); John Naber, Goshen, KY (US); Roger King, Hamilton, OH (US)

(73) Assignee: BioLink Systems, LLC, Covington, KY (US)

( * ) Notice: Subject to any disclaimer, the term of this patent is extended or adjusted under 35 U.S.C. 154(b) by 0 days.

(21) Appl. No.: 16/714,709

(22) Filed: Dec. 14, 2019

(65) Prior Publication Data

US 2020/0113746 A1    Apr. 16, 2020

Related U.S. Application Data

(63) Continuation of application No. 16/127,900, filed on Sep. 11, 2018, now Pat. No. 10,561,541.

(51) Int. Cl.
*G08B 21/00* (2006.01)
*A61F 13/42* (2006.01)
*A61F 13/15* (2006.01)

(52) U.S. Cl.
CPC ........ *A61F 13/42* (2013.01); *A61F 13/15585* (2013.01); *A61F 2013/424* (2013.01)

(58) Field of Classification Search
CPC ................. G08B 21/00; A61F 13/42
USPC ........ 340/603, 604, 605; 604/361, 632, 366, 604/368; 422/82.07
See application file for complete search history.

(56) References Cited

U.S. PATENT DOCUMENTS

| | | | |
|---|---|---|---|
| 7,053,781 B1 | 5/2006 | Haire et al. |
| 7,977,529 B2 | 7/2011 | Bergman et al. |
| 7,996,148 B2 | 8/2011 | Bergman et al. |
| 8,145,422 B2 | 3/2012 | Bergman et al. |
| 8,788,195 B2 | 7/2014 | Bergman et al. |
| 9,107,776 B2 | 8/2015 | Bergman et al. |
| 9,224,102 B2 | 12/2015 | Bergman et al. |
| 9,283,123 B2 | 3/2016 | Bergman et al. |
| 9,314,381 B2 | 4/2016 | Bergman et al. |

(Continued)

*Primary Examiner* — Tai T Nguyen
(74) *Attorney, Agent, or Firm* — Chris Tanner; TannerPatent.com

(57) ABSTRACT

Various methods for detecting moisture in briefs compatible with high volume manufacturing are disclosed. The embodiments herein facilitate protection of the method of adding moisture sensing to a diaper, but could also be used to add sensing to pads and bandages. The primary design intent is optimal moisture detection and low per unit cost. Electrodes within a garment measure electrical properties of the electrodes to determine if the item has contacted moisture. The target moisture is urine, however, other sources and types of moisture can also be sensed. Additional analysis capabilities can be added by selecting particular electrodes or add materials that may react with chemical components of the moisture. Applications of the research Include monitor of incontinence using smart brief (e.g. diaper); monitor perspiration, bleeding, or failure of the protective garment; and monitoring exposure of an item to moisture, including but not limited to inanimate items.

18 Claims, 15 Drawing Sheets

(56) References Cited

U.S. PATENT DOCUMENTS

| | | | |
|---|---|---|---|
| 9,646,073 B2 | 5/2017 | Bergman et al. | |
| 9,665,639 B2 | 5/2017 | Bergman et al. | |
| 9,713,554 B2 | 7/2017 | Bergman et al. | |
| 9,913,608 B2 | 3/2018 | Bergman et al. | |
| 2008/0057693 A1* | 3/2008 | Tippey | H05K 3/4084 |
| | | | 438/597 |
| 2014/0079874 A1* | 3/2014 | Agari | H01L 51/0004 |
| | | | 427/66 |
| 2014/0371702 A1* | 12/2014 | Bosaeus | A61F 13/42 |
| | | | 604/385.01 |
| 2016/0095758 A1 | 4/2016 | Haire et al. | |
| 2016/0116427 A1* | 4/2016 | Laurenson | G01N 27/327 |
| | | | 422/82.01 |

\* cited by examiner

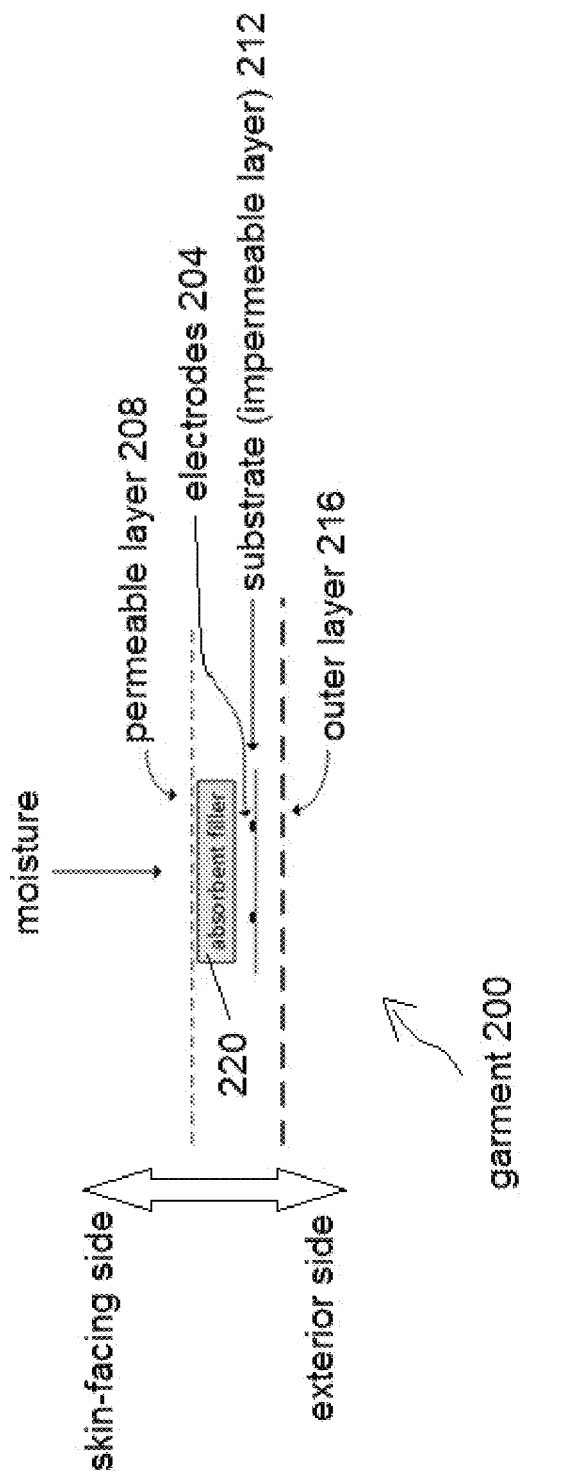
FIG. 2A (cross-sectional view)

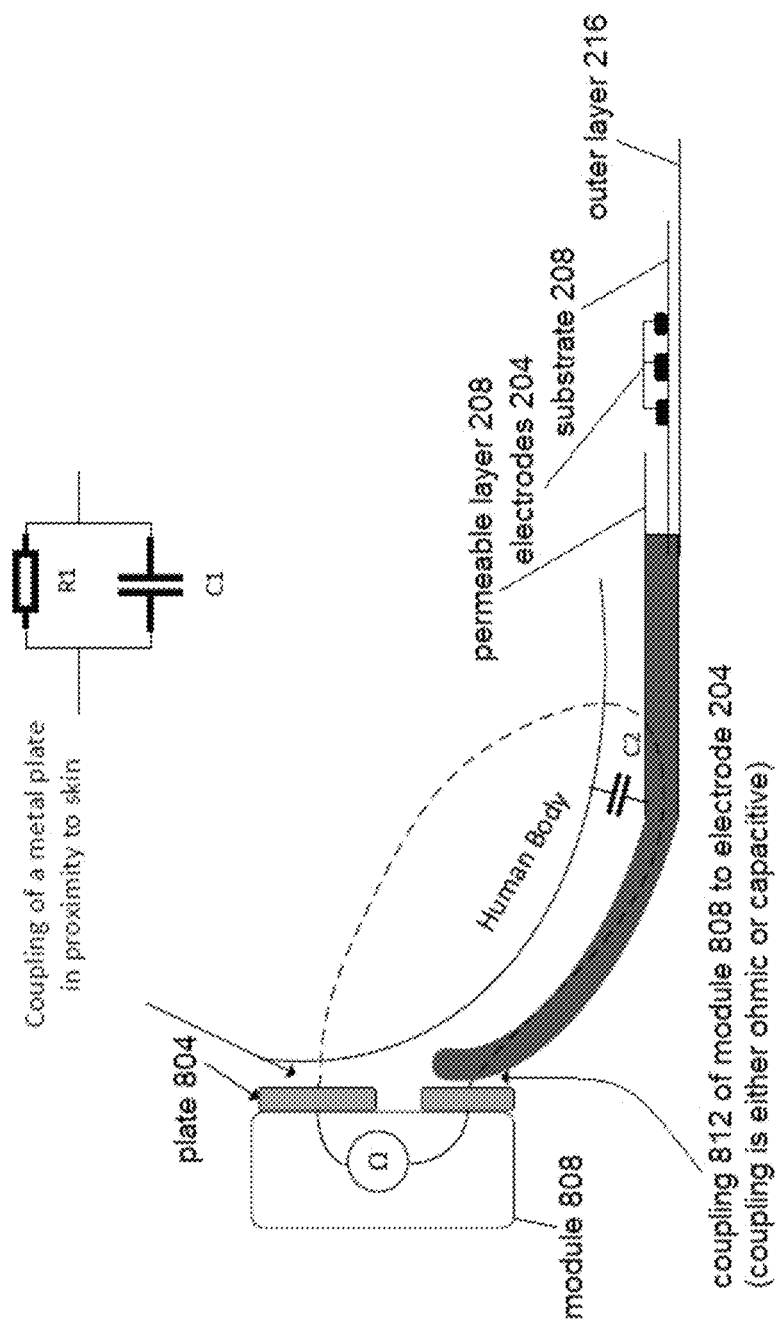
FIG. 8A (dry condition, unwetted, no moisture)

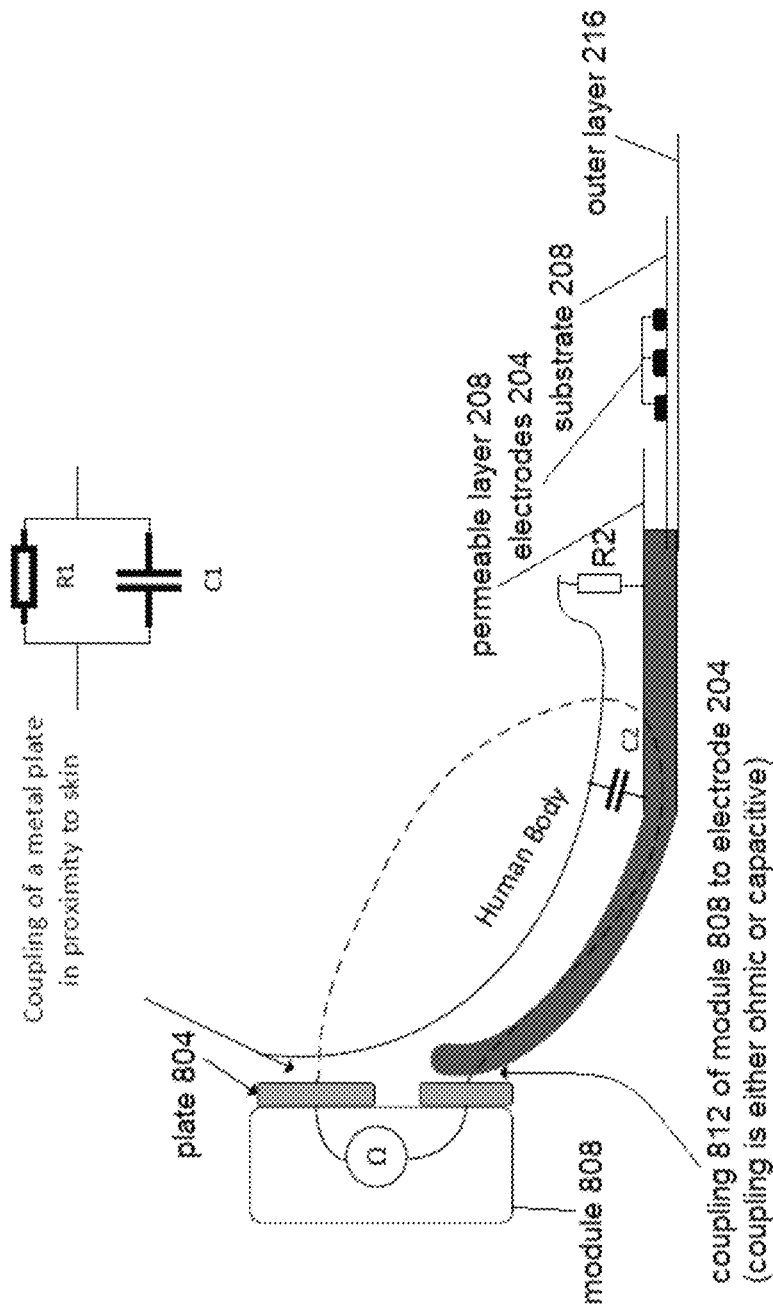
FIG. 8B (wetted condition)

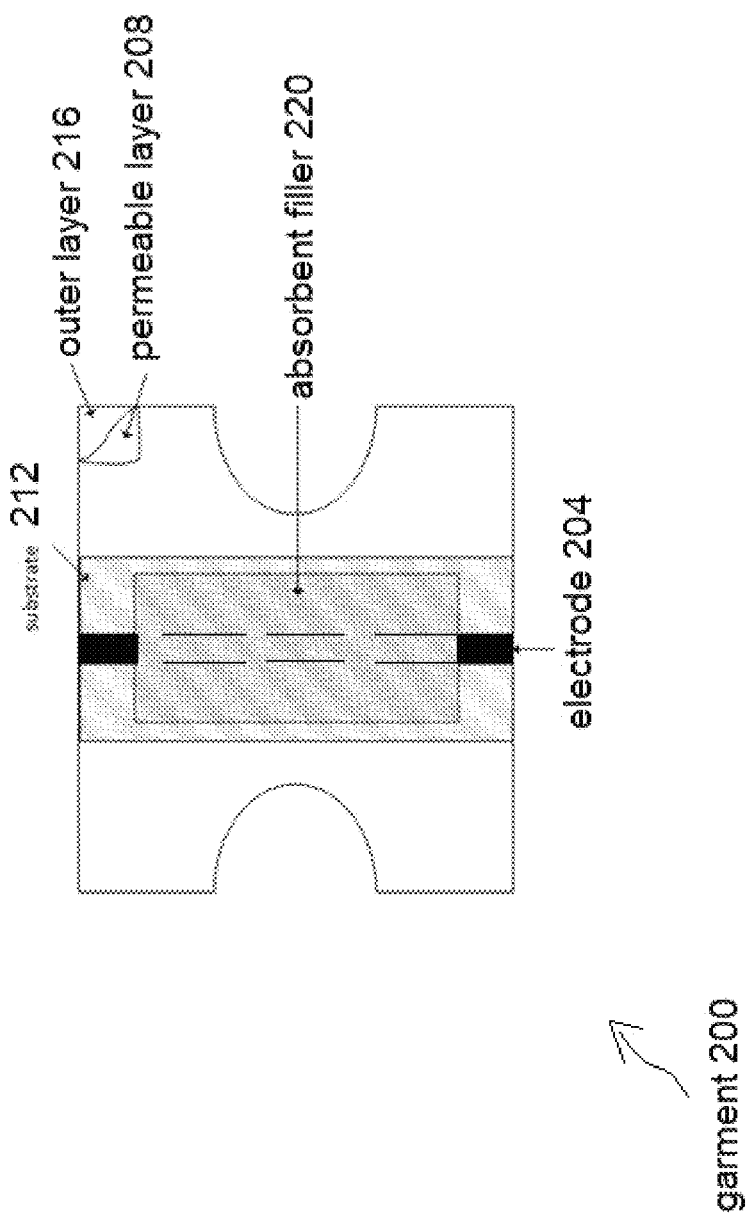
FIG. 9 (human body is the 2nd electrode)

scanning the one or more electrodes thereby detecting whether continuity exists between the one or more contacts connected to the one or more electrodes,  a low resistance measurement indicating multiple contacts are on one electrode, 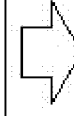 an open circuit measurement indicating the contact is not on the electrode or the electrodes are dry, and a measurement value consistent with moisture indicating the contacts are on multiple electrodes and that moisture is present.

FIG. 13

GARMENT MANUFACTURING SYSTEM AND METHOD

BACKGROUND OF THE INVENTION

A shortcoming of existing embodiments of conductive garments is that incorporating conductive threads or fibers into clothing or other textile or paper products may not compatible with manufacturing in high volume. Consequently, a system and method for inclusion of conductive inks and other materials into clothing or other textile or paper products, for the purpose of sensing moisture, where that system is compatible with high volume manufacturing systems, is desired.

SUMMARY OF THE INVENTION

A method of adding sensing of moisture and other characteristics into a garment such as a diaper, incontinence garment, brief, or underwear is disclosed. The techniques described could also be used to add sensing to pads and bandages. The primary design intent is optimal moisture detection and low per unit cost including designs for mass manufacturing considerations. The embodiments place various forms of electrodes within a garment, and then, while the garment is worn, measuring the electrical properties of the electrodes to determine if the garment has contacted moisture. A sensor element is located within the garment, and the electrical properties of the sensor element are measured to determine if the garment has contacted moisture. Moisture can include, but is not limited to, bodily fluids or fluids from the environment. This invention could be used for incontinence, sensing perspiration, and detecting failure of protective garments. The invention could also be used for general environmental sensing. An example could be containers or packaging that sense moisture. The target moisture is urine and feces; however, other sources of moisture can also be sensed. Additional analysis capabilities can be added by selecting particular electrodes or additional materials that may react with chemical components of the moisture.

The embodiments herein include detection of moisture in an item worn by or placed near a person. Most often this will be a disposable diaper, incontinence garment, brief, or underwear, although embodiments of the combination\system disclosed herein could potentially be used in pads and bandages, and detect types of moisture other than incontinence.

Two design goals are optimal detection and low per unit cost. Applications of the embodiments herein include but are not limited to monitoring of incontinence using smart brief (diaper); monitoring perspiration, bleeding, or failure of protective garment; and monitoring exposure of an item to moisture.

The embodiments herein will accommodate both infant and adult versions, as well as versions used in institutions such as nursing homes, but also in-home versions.

BRIEF DESCRIPTION OF THE DRAWINGS

FIG. 2A shows a cross-sectional view of an embodiment of a garment.

FIGS. 8A, 8B, and 9 show an arrangement of electrodes suitable for capacitive measurement.

FIG. 13 is a flowchart showing a method of using the embodiments.

DETAILED DESCRIPTION OF THE PREFERRED EMBODIMENTS

The following definitions will apply throughout this disclosure.

Garment: A diaper, incontinence device, brief, underwear, or other article of clothing, bandage, or pad containing electrodes.

Module: An electronic device attached to the garment and containing a power source, sensing circuit, and communication circuit.

Electrode: A conductive path connecting the module to a location within the garment being sensed. Two or more electrodes may be used. The electrodes may be the same or different material. Electrodes may provide both connection and sensing functions.

Moisture: A deposition of a single or combination of bodily or other fluids. External sources of moisture may also be sensed.

Substrate: The layer that contains the electrodes.

Figure 1:
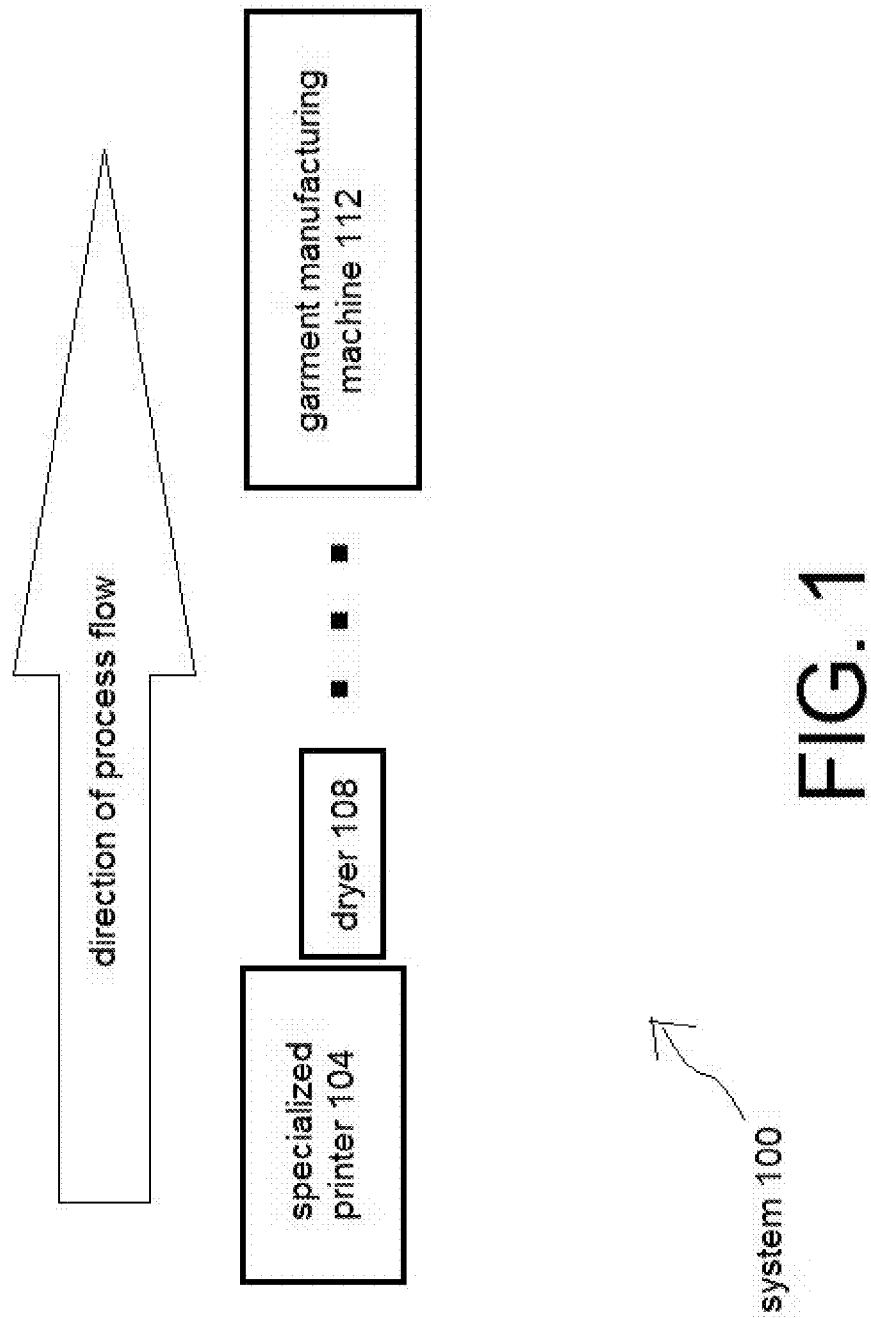
FIG. 1 shows an arrangement of a garment-manufacturing system according to an embodiment.

Contacts: a type of electrical connection to the electrodes, e.g. potentially a place to locate wires or sensors FIG. 1 shows a (simplified) arrangement of a system 100, in which one or more specialized printers 104, each with a dryer 108 at the back end, work in conjunction with a garment manufacturing machine 112 to create various embodiments of the garment 200 discussed herein. In an embodiment, the specialized printer 104 is a flexographic printer, although other types of printers may also be used. The garment manufacturing machine 112 is intentionally shown to be separated from the printer 104 and dryer 108 by ellipses, and thus may be in an entirely different geographic location, or may be on the same premises. Further, the manufacturing processes involving the garment manufacturing machine 112 and the printer\dryer 104\108 may occur at totally different intervals of time.

Machines that make garments, such as but not limited to briefs, are often very large (e.g. about a city block long) and produce garments at great speed, e.g. 1-500 units/minute. In an embodiment, the various features described herein are incorporated into a pre-existing garment manufacturing process, except that a pre-printed poly film (substrate) 212 is further included. One advantage of such an arrangement is that using a pre-printed poly film substrate 212 as described herein will not slow down the manufacturing process whatsoever.

Flexographic printing mechanisms are advantageous for low-cost print procedures. Flexographic printing mechanisms are also suitable because they are fast, and flexographic printing presses usually have ample drying capacity tacked on to their back end. As such, flexographic printers can print and dry very quickly, so that the finished pre-printed poly film or substrate 212 can be rolled up and won't block (stick together or transfer print) since it is already dry. This is an important feature for a garment 200 in which management and detection of moisture is a consideration. Flexographic printers are also often implemented in arrangements of multiple print-stations (e.g. printer 104 and dryer 108). However, the embodiments herein are not exclusively limited solely to flexographic printing.

In an embodiment, the flexographic printer 104 prints an electrode 204 onto a poly film (substrate) 212, which is then referred to as a pre-printed poly film (substrate) 212. Afterwards, the dryer 108 performs drying on the combination. Upon being sufficiently dry, the pre-printed poly film (substrate) 212 may be stored, either individually or in groups.

Further, in an embodiment, the pre-printed poly film (substrate) 212 may be (optionally) subject to being re-run through the specialized printer 104 and dryer 108. Such a re-run or re-printing (over-printing) would be at least for the purpose of assuring suitable levels of conductivity, specifically conductivity of the resulting electrode 204. A visual example of such over-printing is shown at least in FIG. 7.

Once the pre-printed poly film (substrate) 212 has completed its processes, including over-printing if suitable, then, either at that time, or (more likely) at a later time, and potentially in a different facility, the pre-printed poly film (substrate) 212 is fed into the garment manufacturing machine 112 as a pre-printed assembly. As part of that feeding process, the pre-printed poly film 212 can be, for example, located at a bottom of a garment 200, underneath the absorbent mass 220. A breathable outer layer 216 is the portion of the garment 200 which is positioned furthest from the human body.

Figure 2B:
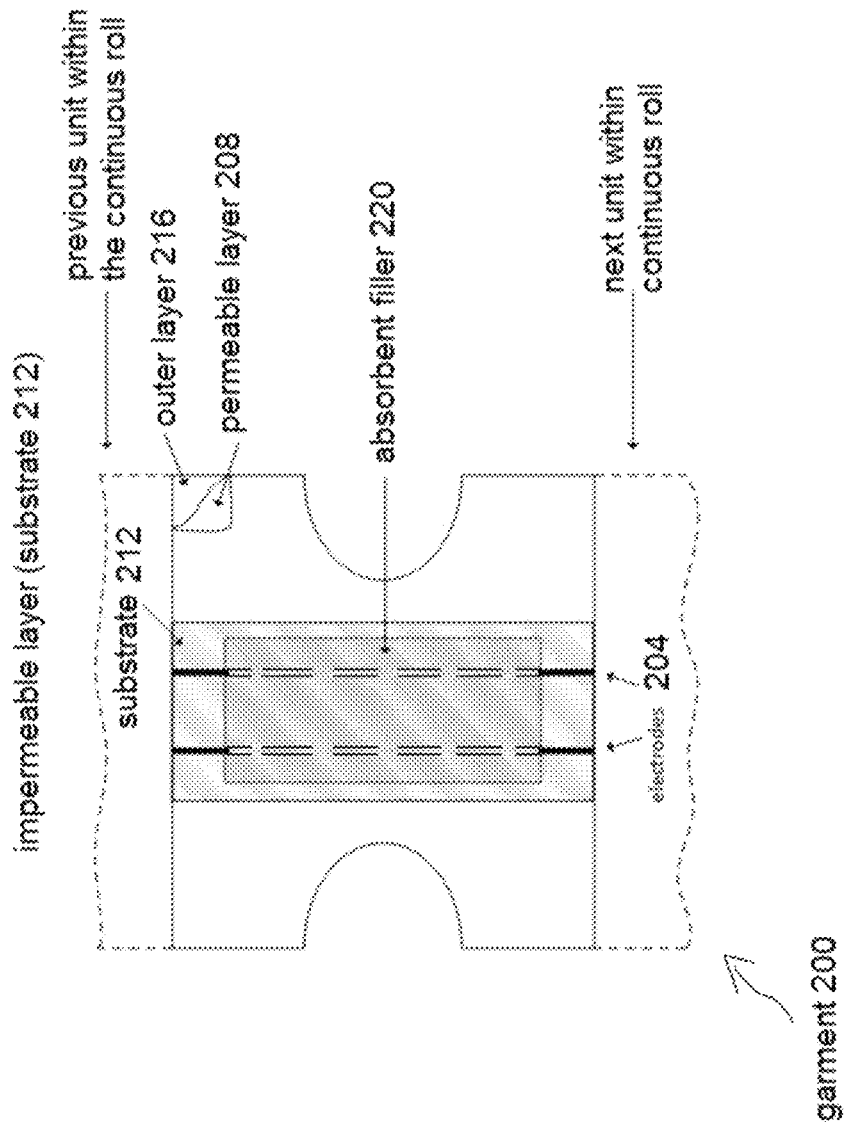
FIG. 2B shows a parallel pattern integrated within a garment in a continuous roll method.

An non-limiting example of such an arrangement of a garment 200 is shown at least within FIGS. 2A and 2B. This location is chosen for being optimal to prevent the moisture, e.g. urine/feces from soaking thru to a bed, chair, or other surface. The pre-printed poly film (substrate) 212 does not get in the way of or cause any problems for the garment manufacturing machine 112 as the film (substrate) 212 is no thicker & no stiffer than the plain poly that is conventionally used. It is important to note that the embodiments shown in FIGS. 2A and 2B are for example only, and the embodiments herein should not be considered as limited thereto.

FIG. 2B illustrates what is meant by "continuous roll", where a roll of garments are shown separated by dashed lines. As the garments 200 are manufactured, the raw materials are combined in a continuous fashion. Most of the layers of the garments are initially on rolls, and they are introduced into the process at the appropriate time. The absorbent mass (filler) 220 is introduced into the manufacturing process in the form of "fluff" (raw fibers) which are later formed into various shapes which fit the human anatomy. This mass is laid down on the pre-printed poly film (substrate) 212, and then nonwoven layers are put below it in the garment, and then more nonwovens are put on top of the absorbent mass 220, to hold the absorbent mass 220 in place.

Various other cuts, and adhesive tabs are added while the garment 200 is still in "roll form". The last thing that happens is the properly layered garment 200 is cut to the proper length and folded. This is important because the continuous strips of conductive ink (electrodes 204) are then completely encapsulated within the garment 200. At a top and bottom edge where the garment 200 is cut at the end of the manufacturing process, there is a thin nonwoven material on top of the conductive ink, and the pre-printed poly film (substrate) 212 and perhaps another nonwoven material underneath. This is the composite through which a conductive connection is made.

Figure 3:
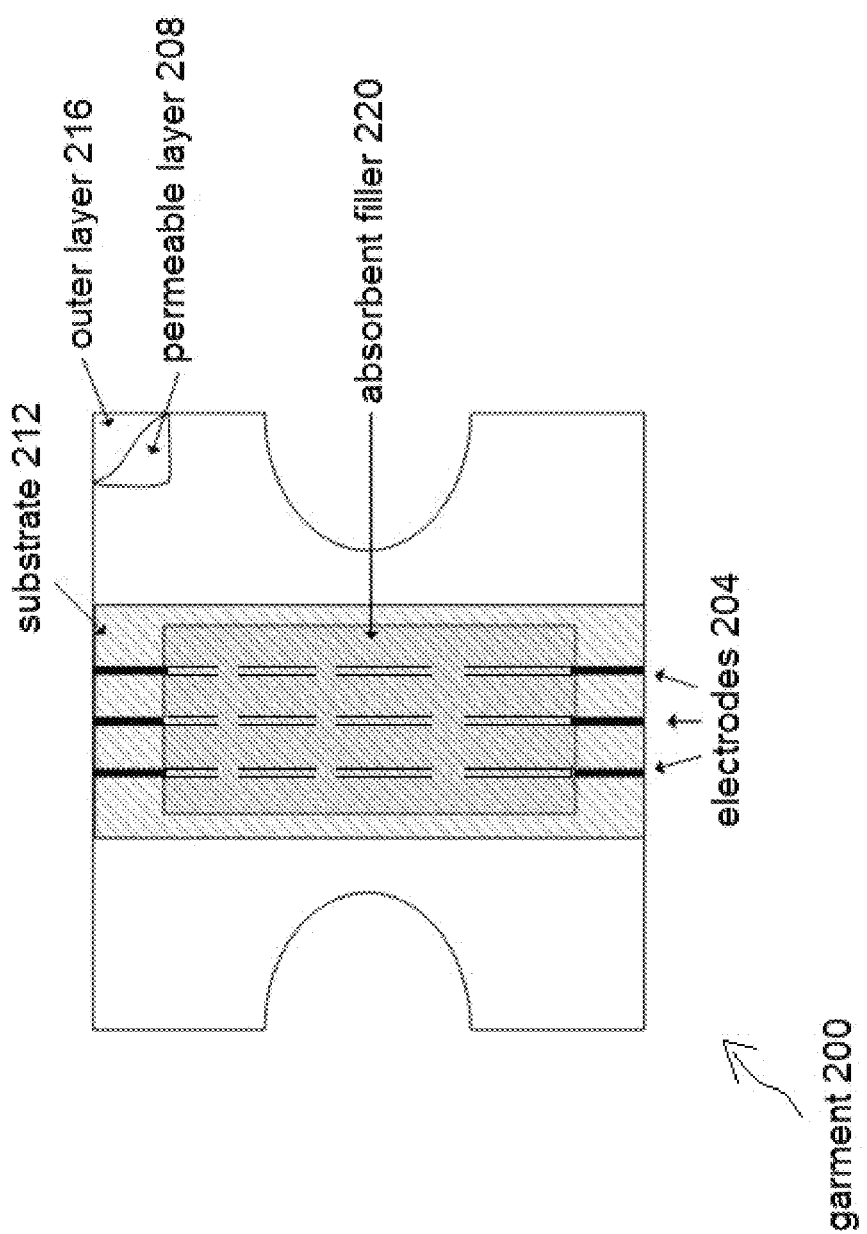
FIG. 3 shows an example pattern similar to FIG. 2, except using three electrodes.
Figure 4:
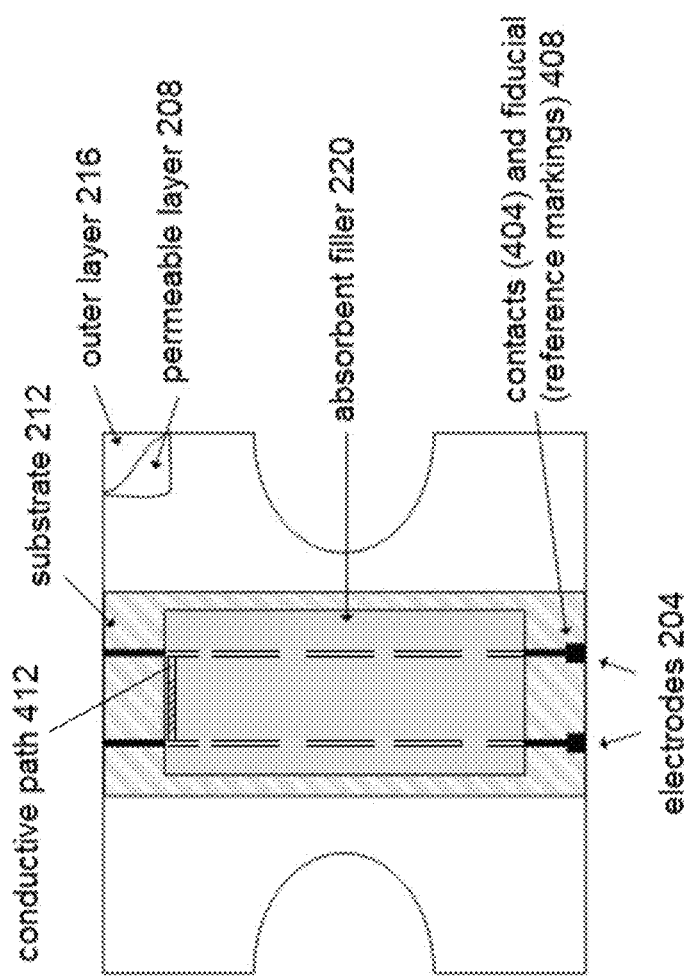
FIG. 4 shows large contact blocks being used as fiducials (e.g. alignment markers).
Figure 5:
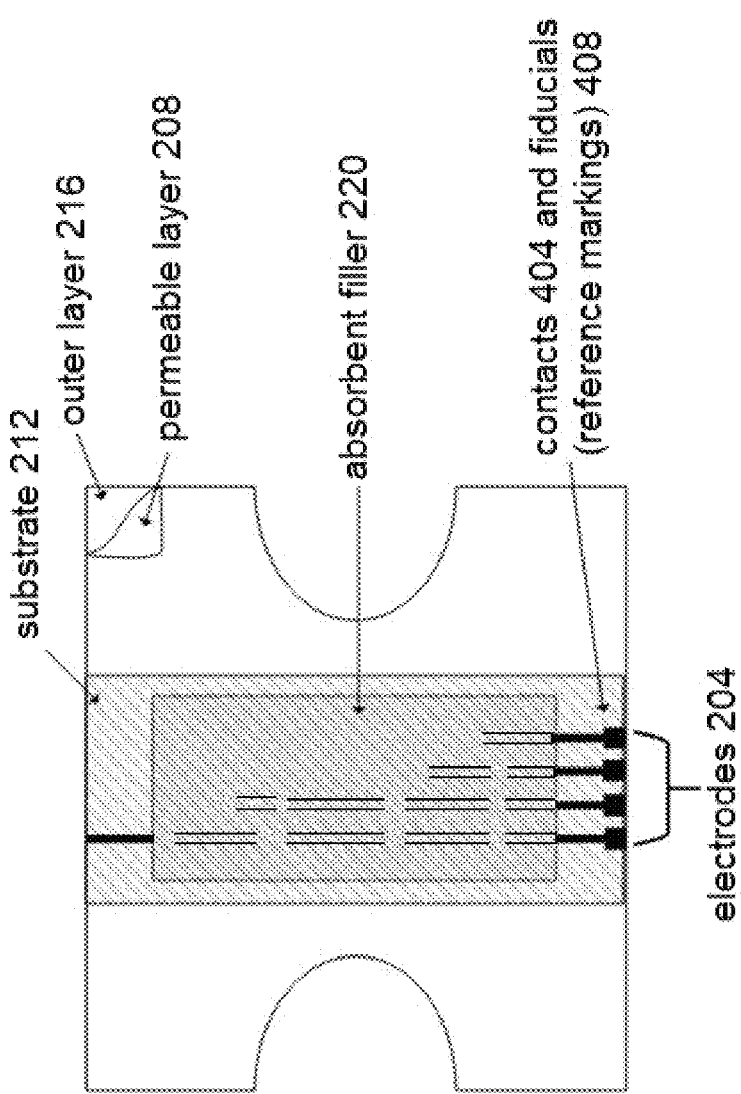
FIG. 5 is a four-electrode design used to measure the size of a wetted area.

Within the embodiments of the garment 200 shown in e.g. FIGS. 2B, 3, 4, the electrodes 204 are shown extending all the way to the edge of the substrate 212. However, this is for example only, for clarity and ease of illustration, but should not be considered limiting. It is not necessary that the electrodes 204 always be positioned this way. FIG. 5 shows an examples where some of the electrodes do not reach all the way to the edge of the substrate 212.

Regarding the conductive inks used to form the electrodes 204, the optimal conductive ink formulation was arrived at only by extensive experimentation and testing. First, the conductive material has to be low-cost, in order to avoid driving up the prices of the completed garments 200. One way to achieve this is using carbon black, which is inexpensive and used commonly in the ink industry as a colorant. The problem is that conventional solvent systems coat the black fibers, so that their conductivity is diminished. To address this, extensive experimentation and testing with ink manufacturers, suppliers of chemicals, and suppliers of fiber grinders was performed. Consequently, it became possible to arrive at the proper solvents to form the conductive inks discussed herein.

As stated, the conductive inks are printed onto a poly film (substrate) 212, which afterwards is referred to as a "pre-printed poly" film or substrate 212.

At some point, perhaps immediately, but more likely later, and perhaps in a different geographic location entirely, the pre-printed poly film (substrate) 212 is then included within a manufacturing process of a garment 200. The width of the pre-printed poly film or substrate 212 is typically 40-50", and the embodiments herein are capable of printing multiple widths at once. As shown for example in FIGS. 2A-2B, the electrodes (AKA conductive strips) 204 are printed parallel to the machine direction, and continuously. The electrodes 204 may be ¼" wide and 2" apart, but this is an example only and should not be considered limiting. The pre-printed poly film 212 is trimmed to the exact width used in the garment 200, and is then delivered to the garment manufacturing machine 112. As such, the garment manufacturing machine 112 incorporates the pre-printed poly film 212 as a feeder component, similarly to how that machine 112 might incorporate the plain poly that is conventionally used in their various garment products.

In an example embodiment, the pre-printed poly film (substrate) 212 is configured to a predetermined width which conforms to a width within the garment 200 being manufactured. It is important to note that the garment-manufacturing machine 112 can use multiple widths simultaneously. In an embodiment, it is possible to arrange the electrodes 204 to be parallel to a direction of the garment-manufacturing machine 112, although this arrangement is not mandatory. The garment-manufacturing machine 112 continuously produces the garments 200.

FIG. 2A shows a cross-sectional view of an embodiment of a garment 200. FIG. 2B shows a parallel pattern that is integrated with a garment 200 in a continuous roll method. As such, alignment of the electrode substrate is not required along the direction of manufacture. FIG. 3 shows an example similar to FIG. 2A, except using three electrodes.

An alternative to the "no alignment approach" is to align the substrate in the axis of manufacture using fiducials (reference markings). This helps to position the substrate features with other components that make up the garment. FIG. 4 shows an example where large contact blocks are used as fiducials (alignment markings) 408 in order to place a close path pattern in a specific position. This aligned approach aids the manufacturing of designs such as those shown in FIGS. 5 and 6. FIG. 4 also shows a conductive path 412. Under conditions of a predetermined wetness, the conductive path 412 provides an additional electrical path besides that which occurs through the electrodes 204.

Another way to explain it: the conductive path 412 bridges the two long electrodes 204. Various of the other embodiments described herein use an open path, however FIG. 4 is a closed path. In those embodiments using open patterns, a dry garment 200 with dry electrodes 204 can be looked at as a type of open circuit. When wetted, the moisture bridges the pattern of electrodes 204.

Conversely, the closed pattern electrodes 204 of FIG. 4 would measure a resistance even when dry. That dry resistance may be just the ink-materials resistance within the electrodes 204 and the conductive path 412. When wetted however, the total resistance would decrease some amount since the moisture is connected in parallel with the path 412 of the electrodes 204. One advantage of such a closed path design is the connection of the module 808 (not shown in FIG. 4) to the electrodes 204 can be verified simply by measuring resistance. Additionally, breaks or mis-prints or ruptures/failures/cracking of the electrodes 204 can be detected.

Moving on to disadvantages, one disadvantage of the embodiment in FIG. 4 is loss of measurement sensitivity, and a requirement to align the electrodes 204 with the edges of the substrate 208. As stated elsewhere, for roll to roll (continuous roll) manufacturing, a design that does not require alignment may be preferable.

Figure 6:
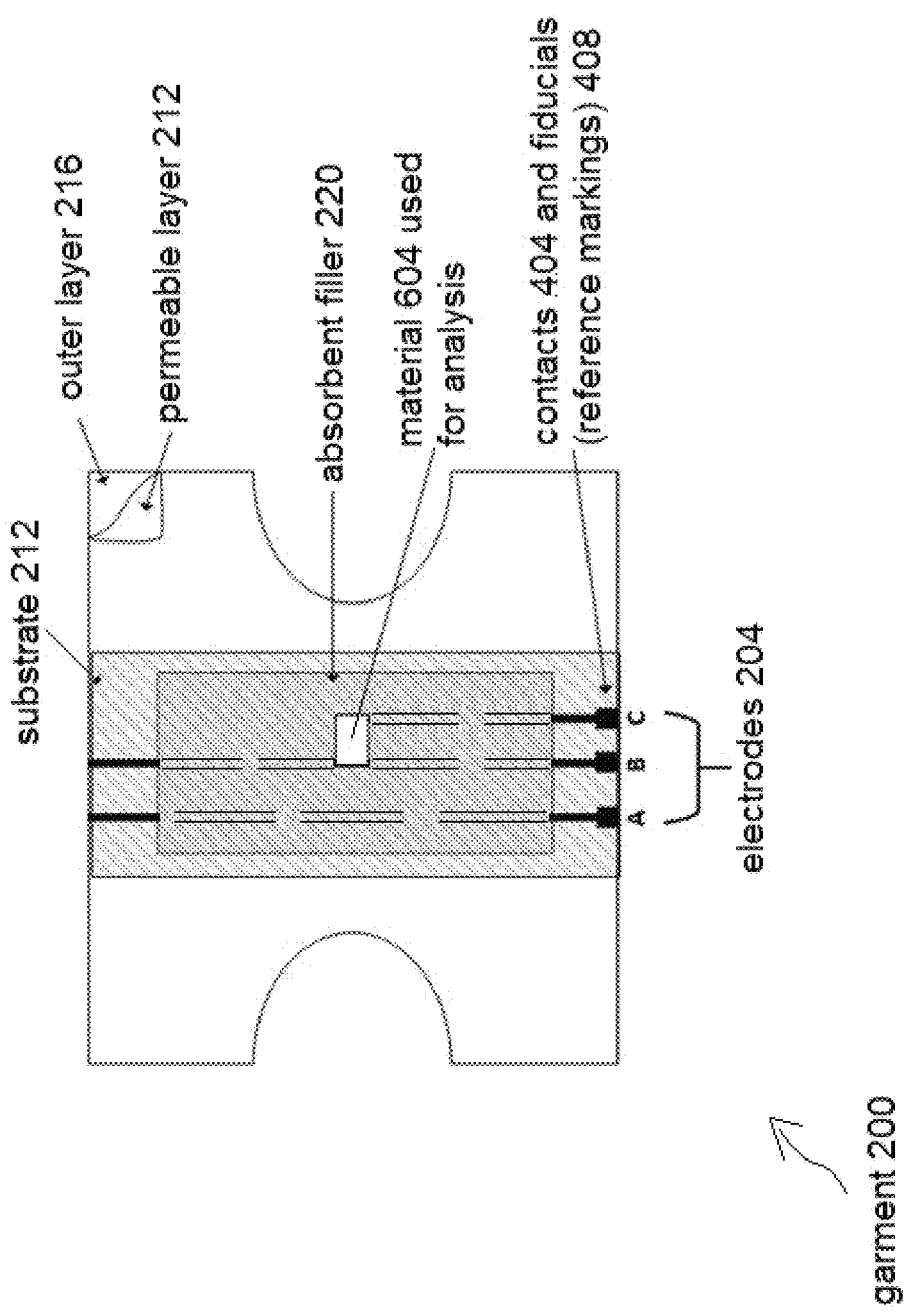
FIG. 6 shows a three-electrode design used to sense moisture and perform analysis using a feature placed in a particular location.

FIG. 5 is a four electrode design used to measure the size of a wetted area. Similarly, FIG. 6 shows three-electrode design used to sense moisture and perform analysis using an analysis feature 604 placed in a specific, predetermined location of the garment 200.

Description of Selected Elements within the Embodiments

1. Electrodes 204 (not Limiting, not a Comprehensive List):

The sensor elements (electrodes 204 and conductive path 412) are conductive elements which may have either a positive or negative response to moisture. For example, resistance may increase when exposed to moisture, or resistance may decrease when exposed to moisture. The response of the material may change depending of the composition of the contacting material. Both DC and AC measurements or other forms of applied voltage including cyclic voltammetry over both positive and negative voltages may be made to detect the presence of moisture or the properties and components of the moisture.

Conductive materials may be used to form the electrodes 204. These conductive materials comprise metals, carbon, compounds, or any material that will conduct-in a dry or wetted condition. The conductive materials may be included in ink for various types of printing, paint, thread, film of various materials, etc. The conductive materials may also be blended with non-conductors for deposition, handling, and improved durability. An insulating layer may be used with the conductive materials. Hydrophilic and hydroscopic materials such as cellulose may be added to improve detection characteristics of the conductive element. Dissimilar materials may also be used to obtain a response different from those obtain from a single material type.

2. Deposition Methods:

Electrodes may be deposited onto the substrate 312 using one or more of rotogravure, flexographic printer (as mentioned), ink jet, offset, screen, extrusion, or xerography printing methods. The electrodes 204 may be made also be made of a material that is placed on, in, or through the substrate 212. Examples of the latter are conductive tape, thread, or wire.

Figure 7:
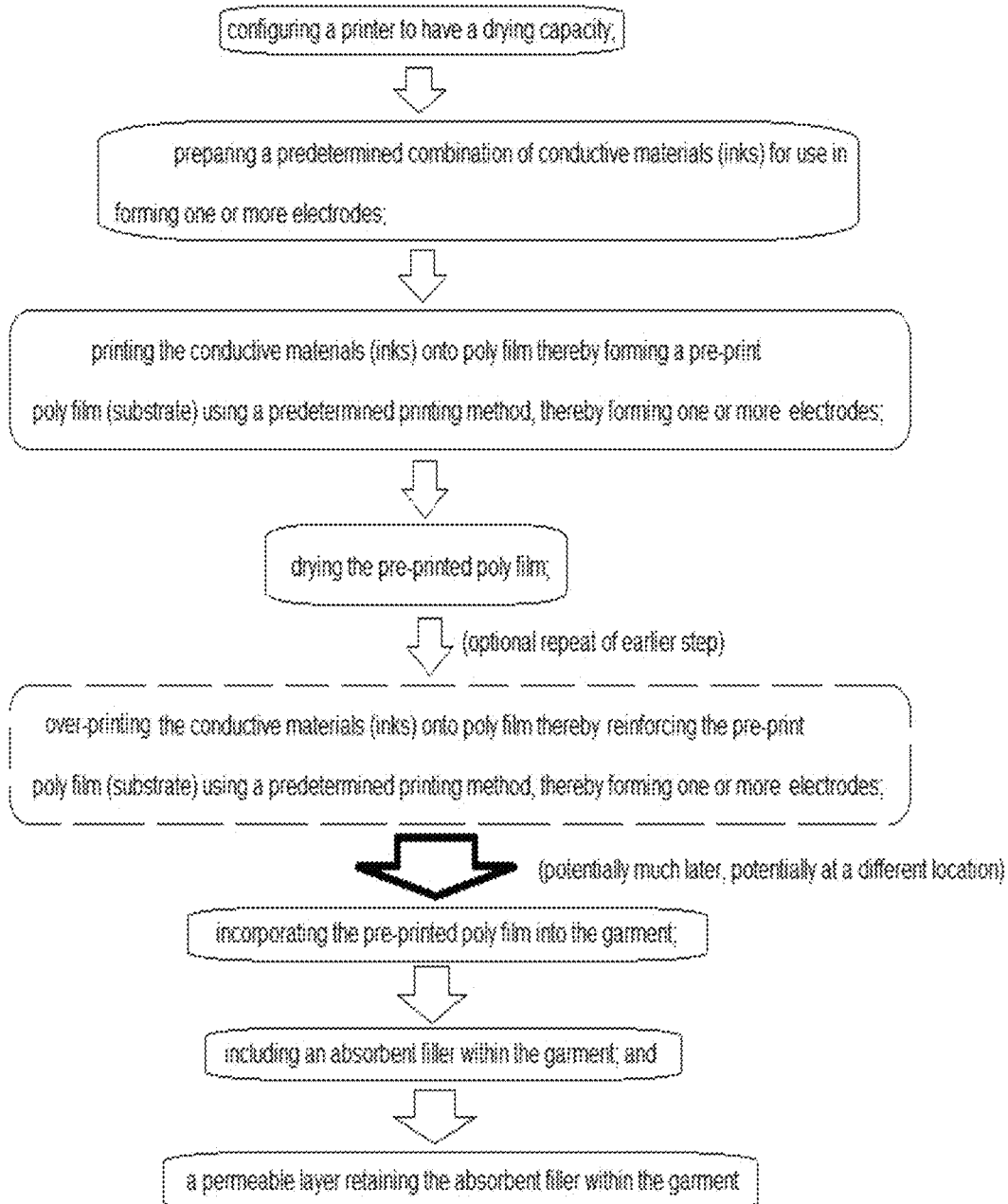
FIG. 7 is a flowchart showing a method of manufacturing the embodiments.

FIG. 7 shows a flowchart of a method of assembling a garment 200.

3. Patterns:

A variety of patterns can be implemented within the electrodes 204, including but not limited to two or more parallel open paths, bridged parallel path, reference markings (fiducials) for manufacturing, process control, or usage.

Another type of pattern is referred to as "continuous path". Within continuous path arrangements, a parallel set of two or more electrodes 204 may be used on the substrate 212 to connect the module location to the sensed area. Such a parallel path can allow the substrate 212 to be integrated with the garment 200 without requiring specific positioning along the axis of the electrode 204 during manufacture. This practice may aid in the "continuous roll" manufacturing discussed earlier, especially where stretchable materials are used.

4. Fabrics Used, and Types of Embodiments.

A combined/integrated manufacturing process starts out creating pre-printed poly films which are born and made solely for use of the various specialized printing, paint, thread, films, and conductive inks disclosed herein. The pre-printed poly films containing the conductive inks are introduced to the fabric forming the garment 200 prior to being cut and shaped into wearable form, that is, prior to being fitted to human anatomy. Nonwoven fabrics, poly films, wood pulp fluff, and SAP (super absorbent polymers) make up the body of the garment 200, with elastic strips, adhesive tabs, etc. applied on the sides.

5. Garment: Diapers, Incontinence Items, Brief, and Underwear.

Within this disclosure, the expression "diapers", "briefs", or "disposable underwear" will be used interchangeably with the phrase "incontinence garments". Regardless of the specific item, all embodiments discussed herein will be manufactured using some variation of one or more conductive strips.

6. Single-Use Items, No Laundry

All embodiments discussed herein will be disposable. In other words, it is intended that there will be no laundering of the garment 200. Whether the garment 200 is in the incontinence diaper format or the briefs (underwear) format, the item will be single-use, disposable, and not intended to be laundered or re-used.

Another advantage is that it is possible, in some embodiments, to reduce the thickness of the absorbent filler 220. This is possible because when the embodiments herein are properly implemented, the active, real-time monitoring for wetness that occurs will limit how long a person will have to wear a wet garment/diaper.

Potential Sensing Approaches (Non-Limiting, not a Comprehensive List)

Moisture Approach 1: Moisture sensing via conductivity. Moisture is sensed by measuring the resistance between two conductive paths. When moisture is present between these paths, the resistance can, for example, decrease. The value of resistance can be, for example, a function of the sheet resistance of the parallel conductors, the distance from the measurement connection to the moisture, the conductivity of the moisture applied across the paths, and for some material, the voltage applied to measure the resistance.

Moisture Approach 2: Measure current generated by the detected moisture: An electrolyte applied to dissimilar conductors may generate current. In this approach, the electrolyte could be urine that when contacting dissimilar conductors creates a voltage that is sensed. A dry electrolyte could also be placed near or with the conductive elements. Moisture would mix with the dry electrolyte to form a more effective solution.

Moisture Approach 3: Electrodes that dissolve in the presence of moisture can also be used to sense that moisture. This approach would require a closed path so that resistance would be measured in a dry condition. In an embodiment, as moisture dissolves the electrode, the resistance would increase. A material that completes the circuit path might be designed to respond to moisture in general or a component of the moisture. A combination of open and closed path electrodes as shown in FIG. 6 could be used. The open electrode arrangement (A to B) would sense the presence of moisture, while the closed path (B to C) might sense a secondary component of the moisture.

Moisture Approach 4: The approaches 1-3 have used multiple electrodes in the garment to sense moisture. However, it is possible to use the human body as part of the measurement circuit and use a single electrode in the garment 200.

An example of this is shown in FIGS. 8A and 8B show an additional embodiment for connecting between the module 808 and electrodes 204 embedded in the garment 200. Previous approaches (e.g. FIGS. 3, 5, 6) used ohmic contacts between the electrodes 204 and the module 808 (shown in FIG. 8, not shown in FIG. 3, 5, or 6) that is clipped onto the garment 200. In contrast, the embodiment of FIGS. 8A-8B uses the human body as one of the electrodes. The module 808 makes connection to the human body using a metal plate 804 that provides an electrical path via resistive (R1), capacitive (C1), or both connection. The electrode 204 is coupled to the module 808 by either ohmic contact or capacitive coupling, or both.

The module 808 measures the impedance properties between the human body and the electrode 204. Either an AC and DC measurement, or both, may be utilized, depending on the details of the specific design. As shown in FIG. 8A, when the garment 200 is dry, the natural impedance between the human body and the electrode 204 is quite high, potentially close to infinite. That is why R2 is not even shown in FIG. 8A, because the resistance may be so high as to not be worth depicting. In both FIGS. 8A and 8B, R1 and C1 refer to resistance and capacitance of the plate 804 to the body.

Moving on to FIG. 8B, when the garment 200 is wetted, the impedance from human body to the electrode 204 is reduced because the capacitance of C2 is increased, and resistance R2 may be present. R2 resistance will depend on the absorption capabilities of the materials used to form that specific embodiment of the garment 200.

One advantage of the FIGS. 8A-8B approach can be the reduction or elimination of ohmic contacts as well as the use of only a single electrode 204 within the garment 200.

To rephrase, FIG. 8A shows that in a dry, unwetted condition, the human body will still have a naturally occurring amount of body capacitance C2. The module 808 electrically connects to the human body using resistive or capacitive coupling and to the electrode 204 through resistive or capacitive coupling. During or after wetting of the garment or thereafter, the resistive and capacitive coupling between the body and garment electrode would change. That is why R2 is shown in FIG. 8B, but is not shown in FIG. 8A. Such a change in coupling could be detected by either AC or DC measurements including pulsed DC., or other forms of applied voltage including cyclic voltammetry over both positive and negative voltages.

In both FIGS. 8A and 8B, the plate 804 is shown as two separate physical pieces. However, the plate 804 can also be a single unified piece. If capacitive coupling is used for both the human body and connection of electrode 204, then separation of the plates 804 is desired. If an ohmic contact is used for the electrode 204, then only one plate 804 would be needed.

Moisture Approach 5: Sensing components of body fluids: A reactive material may be placed in contact or near one or more electrodes 204 for the purpose of sensing the specific components of a fluid. Multiple materials may be used to sense multiple components or to serve as calibration or as reference values useful for improving accuracy of other measurements. The reactive materials may be chosen based on their properties with respect to e.g. urine, fecal matter, sweat, blood, or other bodily fluids.

For example, an enzyme selective electrode 204 might be used for glucose detection. A sensor patch including a semi-permeable membrane, glucose oxidase enzyme, and electrode could be placed in the area of the garment 200 that contacts urine. When urine is detected by conductivity, a measurement of the sensor patch could be initiated for determination of glucose content. Another example would be for the materials to have the ability to measure nitrites, leukocytes, lymphocytes, granulocytes, monocytes, and macrophages to indicate if the person has an active infection present.

FIG. 13 shows a flowchart of an example method of using and operating the garment 200.

Potential Materials (Non-Limiting, not a Comprehensive List):

1. Conductive: Electrodes may contain metals, carbon, or materials that can conduct electricity. This include ink, paints, polymers, ionic compounds, or combinations. Each electrode may have a different composition.

2. Catalyst: Electrodes may contain materials that react with moisture or components within moisture.

3. Dissolvable: Materials may be soluble or insoluble. The solubility of a material may indicate a measurement value or may serve the purpose of providing a substance for a measurement.

4. Hydrophobic or hydrophilic: Hydrophobic or hydrophilic coatings and materials may be used to direct fluid contact. This in turn can contribute to improving measurement accuracy.

5. Binder or Enhancements: Materials may be added to improve wetting, adhesion, durability, resistance to oxidation, flexibility and resistance to cracking, or to aid in manufacturing.

6. Sensors and Power Sources: Both DC and AC measurements may be made to detect the presence of moisture or the properties and components of the moisture, including pulsed DC, or other forms of applied voltage including cyclic voltammetry over both positive and negative voltages.

Potential Substrates (Non-Limiting, not a Comprehensive List):

The substrate can be a paper, fiber, a plastic film, or other material that can form a 'fil' (not a spelling error) of mesh. The substrate can be smooth or contain embossed features to improve deposition of materials. Embossing or patterning of the substrate can be used to improve resistance to broken conductive paths when the substrate is stretched.

Figure 10:
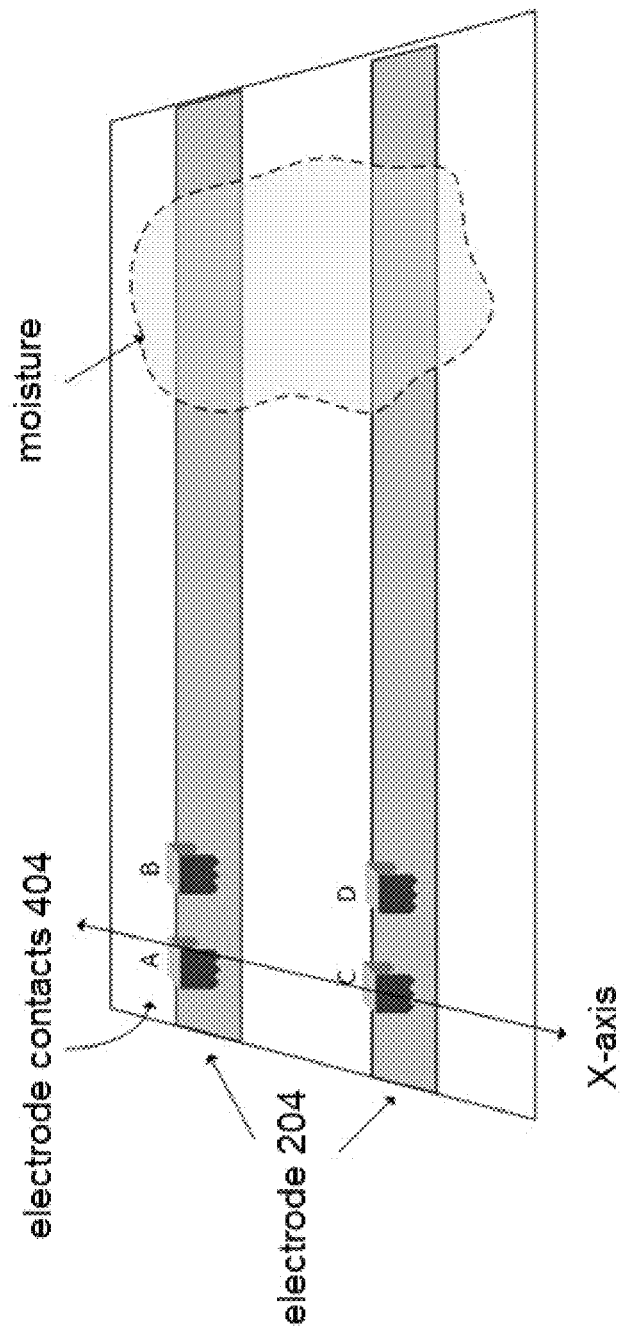
FIG. 10 shows an example of continuity measurement from (A to B) verifying contact to an electrode.

Potential Implementations for the Contacts 404 (Non-Limiting, not a Comprehensive List):

The module 808 (shown in FIG. 8, but not shown in FIG. 1) makes Ohmic contact to an electrode 204 with one or more connections per electrode 204. Two or more connections per electrode 204 allow the Ohmic contact from the module 808 to the electrode 204 to be verified by a continuity measurement on the electrode 204. The example shown in FIG. 10 shows that a continuity measurement from (A to B) will verify contact to the electrode 204 and that the contacts 404 are not offset along the X-axis missing the electrode 204. If a closed loop electrode path is used, continuity can be verified from by measured the path continuity between the AB and CD sets of contacts 404.

The physical connection to the surface of the electrode 204 can be made through the permeable layer 208 that retains the absorbent filler 220. In this embodiment, it is required that the contacts 404 pierce the permeable layer 208. Multiple points on each contact 404 may be used to improve contact reliability. Further, in an embodiment, the physical connections to eh surface of the electrodes 204 can also provide confirmation as to whether the electrical connection to the electrodes is sufficient to convey useful information.

Figure 11:
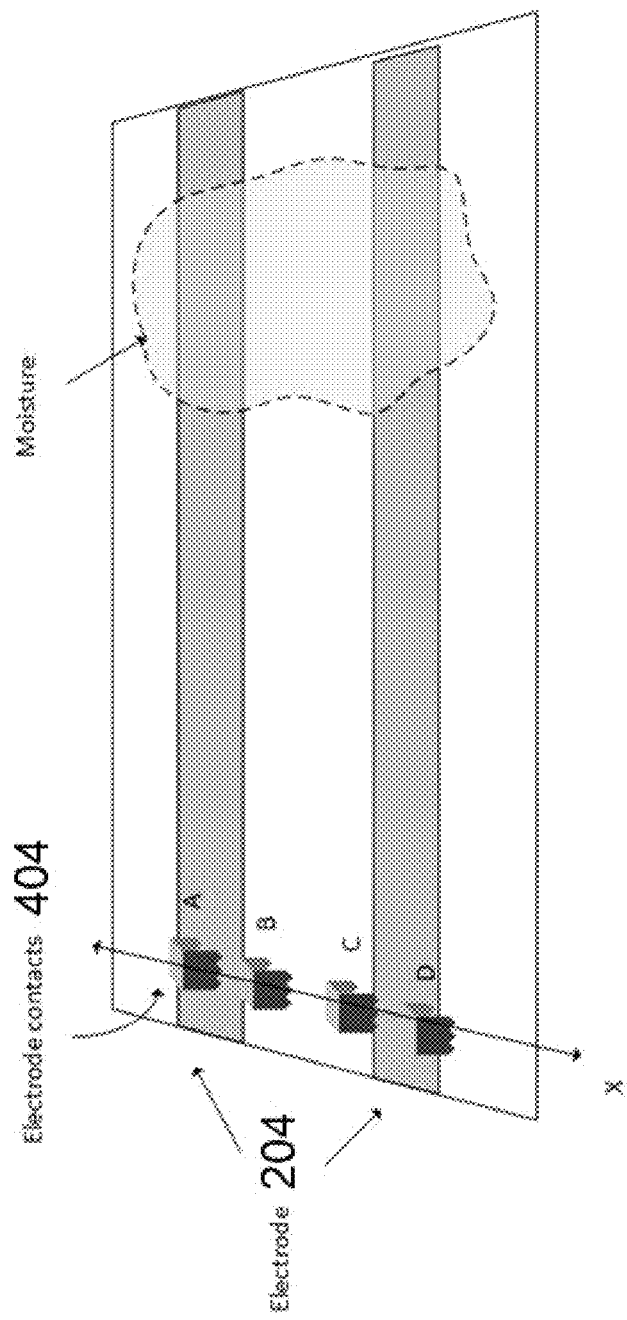
FIG. 11 shows electrode contacts placed along an X-axis, where the electrodes are scanned to detect continuity between contacts.

The contacts 404 can also be placed along an X-axis of a garment 200, as shown in FIG. 11. In this example the electrodes 204 are scanned to detect continuity between the contacts 404. A low resistance measurement indicates multiple contacts $404_{1-n}$ are on one electrode 204. A measurement of open circuit (infinite impedance) would indicate the contact 404 is not connected to the electrode 204, or the electrodes 204 are dry. A measurement value consistent with moisture indicates the contacts 404 are on contacting multiple electrodes 204 and the moisture is present. The method of FIG. 11 also aids the task of aligning the module 808 (not shown in FIG. 11) with the electrodes 204.

A non-Ohmic measurement has the advantage of requiring no direct physical contact with an electrode 204. Instead, capacitive coupling can be used to provide the connection to an electrode 204. The capacitive measurement may be used with one of more electrodes 204 as shown at least within FIGS. 8, 9, and 12.

Figure 12:
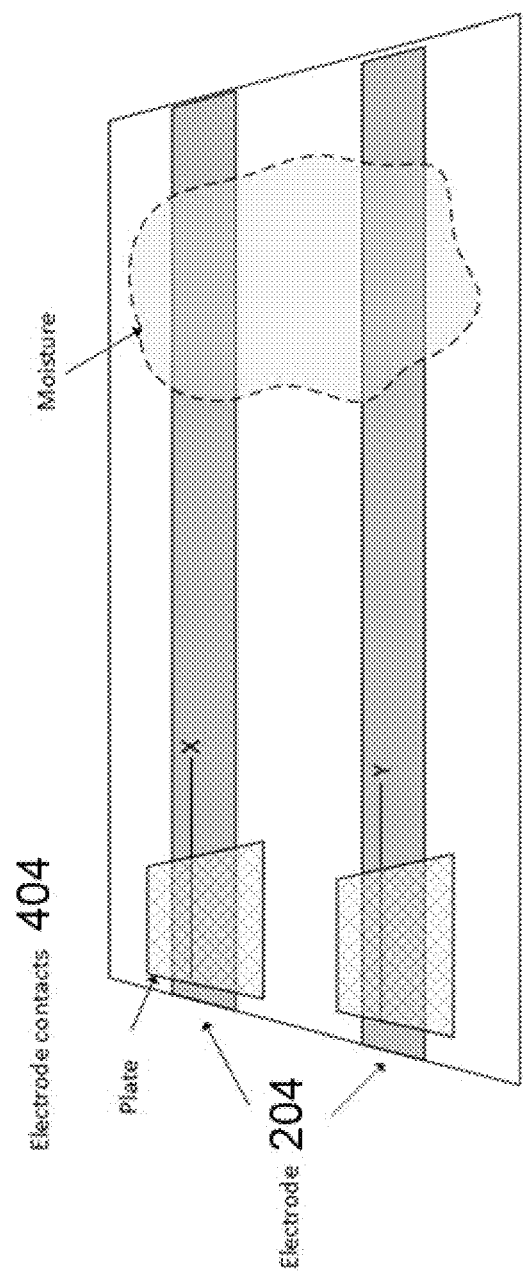
FIG. 12 shows an additional arrangement of electrodes suitable for capacitive measurement.

Specifically, FIG. 12 shows a design where capacitive coupling is used to connect the module to two electrodes. This is different from the configuration shown in FIG. 8 in that the human body is not used as a path for the measurement. Again the advantage of capacitive coupling between the module 808 and electrodes 204 is the elimination of the ohmic contacts. Ohmic contacts may be unreliable, wear out, require too much attention during attachment of the module 808, or complicate the mechanical design of the module 808.

Potential Relationships Between Contacts 404 & Electrodes 204

The following is a non-limiting list of potential implementations of the embodiments herein. These potential implementations are for suggestion only, so that the embodiments herein should not be considered as limited exclusively thereto.

single contact 404 to single electrode 204 scenario: would use a single electrode 204 with one contact 404. There would be a ground path through the garment 200 to a ground pad on the module (e.g. module 808). The garment 200 would have to detect a moisture change at this ground pad, which could potentially utilize an extended probe contact from the module. Alternately, the person wearing it would provide the ground. The latter would require a good electrical connection to human skin. The moisture in the urine would provide the electrical path between the single electrode 204 and the ground contact.

2 contacts 404 to 2 electrodes 204 scenario: can measure the module making acceptable contact to the electrodes 204, e.g. if the electrodes 204 are is in a closed path.

4 contacts 404 to 2 electrode 204 scenario: can measure the module making acceptable contact to the electrodes 204, e.g. if the electrodes 204 are in an open path.

APPENDIX

The following is not a listing of claims. Instead, the following is merely a non-limiting listing of subject matter that could potentially be used in dependent claims in the future. The listing is divided into DEP MANU (potential dependent manufacturing claims) and DEP USE (potential dependent use claims).

DEP MANU locating a dry electrolyte near or within one or more conductive paths;

moisture extracting the dry electrolyte thereby forming a solution suitable for detecting the moisture.

DEP MANU adding materials to the electrodes to improve adhesion, durability, resistance to oxidation, flexibility and resistance to cracking, and to aid in manufacturing;

DEP MANU embossing features into the pre-printed poly film thereby increasing resistance to breakage of the conductive paths when the pre-printed poly film is stretched.

DEP MANU wherein the embossing steps results in reducing noise and increasing comfort for a wearer.

DEP MANU blending the conductive materials with non-conductors thereby increasing deposition, handling, and durability.

DEP MANU locating the pre-printed poly film at an outside of the absorbent filler according to predetermined criteria.

DEP MANU the predetermined criteria being optimal for preventing urine/feces from soaking thru to a bed or mattress pad.

DEP MANU rolling up the dried pre-printed poly film, thereby reducing blocking, sticking together, and transferring of the electrodes printed therein.

DEP MANU at a top and bottom edge, arranging a first thin nonwoven material on top of the conductive material (inks), and a second nonwoven material underneath, thereby creating a composite;

making conductive connections through the composite;

cutting the layered finished garment to the predetermined length; and folding the layered finished garment, thereby completely encapsulating the continuous strips of conductive ink.

DEP MANU the predetermined printing method comprising rotogravure, ink jet, offset, screen, extrusion, or xerography.

DEP MANU the electrodes comprising conductive elements having either a positive or negative response to moisture;

DEP MANU providing a connection to the electrode via capacitive coupling;

DEP MANU including hydrophilic, hydroscopic, and/or super-absorbent materials such as cellulose, thereby improving detection characteristics of the conductive elements;

DEP MANU including two or more dissimilar materials may also be used to obtain a response different from those obtain from a single material type.

DEP MANU the electrodes comprising a material that is placed on, in, or through the substrate;

DEP MANU integrating the substrate within the garment without requiring specific positioning (alignment) along the axis of the electrode and manufacture using a parallel path printing technique, thereby facilitating continuous roll manufacturing;

DEP MANU aligning the substrate in the axis of manufacture using reference markings, thereby positioning the substrate features to match with other components that make up the garment;

DEP MANU applying elastic strips and adhesive tabs on the sides of the garment; DEP MANU applying adhesive tabs to the garment while still in un-cut (roll) form;

DEP USE wherein the garment is single-use, disposable, and not intended or re-used.

DEP USE the resistive and capacitive coupling between the body and garment electrode changing according to the change in moisture;

DEP USE placing a reactive material in contact or near one or more electrodes for the purpose of sensing the components of a moisture condition;

DEP USE using the human body as one of the electrodes;

DEP USE arranging one or more reactive materials to serve as calibration or reference values useful for improving accuracy of the measurements.

DEP USE incorporating a hydrophobic or hydrophilic coatings and materials to direct fluid contact; thereby improving measurement accuracy;

DEP USE applying an electrolyte to dissimilar conductors, thereby generating current;

DEP USE two or more parallel open paths, bridged parallel path, reference markings (fiducials) for manufacturing, process control, or usage.

The invention claimed is:

1. A method of manufacturing a garment, comprising:
preparing a predetermined combination of conductive materials for use in forming one or more electrodes;
forming a pre-printed poly film using a predetermined printing method;
one or more print stations printing the conductive materials onto the pre-printed poly film, thereby forming the one or more electrodes; and
incorporating the pre-printed poly film into the garment;
locating the pre-printed poly film at an away-from-body portion of the garment according to predetermined criteria; and
positioning a predetermined amount of absorbent filler between the body of the wearer and the pre-printed poly film.

2. The method of claim 1, further comprising:
manufacturing the pre-printed poly film of a material selected from a group consisting of paper, fiber, and plastic film.

3. The method of claim 1, further comprising:
locating a skin-facing layer permeable to bodily fluids within the garment at a position closest to a skin of a wearer;

locating an absorbent filler between the pre-printed poly film and the skin-facing layer permeable to bodily fluids.

4. The method of claim 3, further comprising:
testing a finished garment in a live, in-use environment where the garment is worn by a human;
facilitating active, real-time monitoring of the garment for wetness; and
depending on a set of results from the monitoring and testing, in future manufacturing of future garments, reducing a thickness of the absorbent filler.

5. The method of claim 3, further comprising:
forming a physical connection to a surface of the one or more electrodes through a permeable layer that retains the absorbent filler layer;
the contacts piercing the skin-facing permeable layer;
the physical connections to a surface of the one or more electrodes providing confirmation as to whether an electrical connection to the one or more electrodes is sufficient to convey valid electrical signals.

6. The method of claim 1, further comprising:
sensing moisture by measuring a resistance between two electrodes, wherein a value of resistance is selected from a group consisting of
the sheet resistance of the parallel conductors,
the distance from the measurement connection to the moisture,
the conductivity of the moisture applied across the paths, and
the voltage applied to measure the resistance.

7. The method of claim 1, further comprising:
one or more closed path electrodes dissolving in a presence of an amount of moisture within the bodily fluids;
in a garment-dry condition, the one or more closed path electrodes having no resistance;
the resistance across the one or more closed path electrodes increasing as moisture dissolves the one or more closed path electrodes.

8. The method of claim 7, further comprising:
utilizing a combination of open path and closed path electrode arrangements;
the open path electrode arrangement sensing a presence of an amount of moisture within the bodily fluids; and
the closed path electrode arrangement sensing a secondary component of the bodily fluids.

9. The method of claim 1, further comprising:
the substrate containing embossed features to improve the printing of conductive materials onto the substrate.

10. The method of claim 9, further comprising:
the embossing of the substrate improving resistance to breakage of conductive paths within the one or more electrodes in an event the substrate is stretched.

11. The method of claim 1, further comprising:
locating a dry electrolyte near or within the one or more electrodes;
as bodily fluids accumulate within the garment, an amount of moisture within the bodily fluids extracting the dry electrolyte thereby forming a trigger solution suitable for signaling that moisture exists.

12. The method of claim 1, further comprising:
prior to the step of printing, blending the conductive materials with a predetermined amount of non-conductive materials, thereby increasing deposition, handling, and durability during the printing process.

13. The method of claim 1, further comprising:

the predetermined criteria being optimal for preventing urine/feces from soaking thru to a bed or mattress pad occupied by the wearer.

14. The method of claim 1, further comprising:

at a top and bottom edge of the pre-printed poly film, arranging a first thin nonwoven material on top of the one or more electrodes, and a second nonwoven material underneath the one or more electrodes, thereby creating a composite;

making conductive connections through the composite;

cutting a layered finished garment to a predetermined length; and folding the layered finished garment, thereby completely encapsulating the one or more electrodes.

15. The method of claim 1, further comprising:

integrating a substrate within the garment while avoiding specific positioning and alignment along an axis of manufacture of the one or more electrodes; and manufacturing using a parallel path printing technique thereby facilitating continuous roll manufacturing.

16. The method of claim 1, further comprising:

aligning a substrate in an axis of manufacture using reference markings, thereby positioning the substrate features to match with other components that make up the garment.

17. The method of claim 1, further comprising:

fabricating, packaging and marketing the garment to be single-use, disposable, and not to be laundered or re-used.

18. The method of claim 1, further comprising:

arranging one or more reactive materials within the one or more electrodes to serve as calibration and reference values useful for testing and improving accuracy of the electrical measurements produced by the garment.

* * * * *